United States Patent [19]

Essenpreis et al.

[11] Patent Number: 5,770,454
[45] Date of Patent: Jun. 23, 1998

[54] METHOD AND APARATUS FOR DETERMINING AN ANALYTE IN A BIOLOGICAL SAMPLE

[75] Inventors: Matthias Essenpreis, Gauting; Dirk Boecker, Heidelberg; Heinz-Michael Hein, Seeheim-Jugenheim; Hans-Peter Haar, Wiesloch, all of Germany

[73] Assignee: Boehringer Mannheim GmbH, Mannheim, Germany

[21] Appl. No.: 737,135
[22] PCT Filed: May 3, 1995
[86] PCT No.: PCT/DE95/00593
§ 371 Date: Nov. 7, 1996
§ 102(e) Date: Nov. 7, 1996
[87] PCT Pub. No.: WO95/32416
PCT Pub. Date: Nov. 30, 1995

[30] Foreign Application Priority Data

May 19, 1994 [DE] Germany .................. 44 17 639.2

[51] Int. Cl.⁶ .................................................. G01N 21/00
[52] U.S. Cl. .................. 436/164; 422/82.05; 422/82.09; 356/39; 356/300; 356/317; 600/310; 600/322
[58] Field of Search ............................. 436/63, 164, 171; 422/82.05, 82.09; 356/39, 300, 317, 337; 128/633, 664, 665; 600/309, 310, 322

[56] References Cited

U.S. PATENT DOCUMENTS

| | | | |
|---|---|---|---|
| 4,972,331 | 11/1990 | Chance | 364/550 |
| 5,137,355 | 8/1992 | Barbour et al. | 356/342 |
| 5,277,181 | 1/1994 | Mendelson et al. | 600/322 |
| 5,441,054 | 8/1995 | Tsuchiya | 600/310 |
| 5,477,051 | 12/1995 | Tsuchiya | 250/341.1 |
| 5,497,769 | 3/1996 | Gratton et al. | 600/323 |
| 5,507,288 | 4/1996 | Böcker et al. | 600/322 |
| 5,517,987 | 5/1996 | Tsuchiya | 600/328 |
| 5,529,065 | 6/1996 | Tsuchiya | 600/310 |
| 5,551,422 | 9/1996 | Simonsen et al. | 600/322 |

FOREIGN PATENT DOCUMENTS 0 663 591  7/1995  European Pat. Off. .

OTHER PUBLICATIONS

SPIE Proceedings, vol. 1888, Sep. 1993, pp. 248–257, A. Duncan et al, "A Multiwavelength, wideband, intensity modulated optical spectrometer for infrared spectroscopy and imaging".

International Publication No. WO 93/11701 published Jun. 24, 1993.

(List continued on next page.)

Primary Examiner—Jan Ludlow
Assistant Examiner—Maureen M. Wallenhorst
Attorney, Agent, or Firm—Nikaido, Marmelstein, Murray & Oram LLP

[57] ABSTRACT

A method and apparatus for analytical determination of a concentration of an analyte in a biological sample include a series of hardware elements and method steps which perform at least two detection measurements, with each detection measurement including the step of irradiating light at an irradiation site as primary light into the biological sample through a boundary surface. The light is propagated along a light path, and light is detected as it emerges from the biological sample as secondary light through a detection site. The irradiation site and detection site are separated by a measuring distance. At least two detection measurements are performed with at least two different measurement light paths between the irradiation site and the detection site. Each of the detection measurements is a frequency-domain spectroscopic measurement which is performed at at least two different wavelengths of light, and includes a comparison of a phase shift of the secondary light with the primary light as a first measurement variable, and an intensity of the secondary light as a second measurement variable. The method also includes the steps of determining the analyte concentration based upon the first and second measurement variables.

51 Claims, 6 Drawing Sheets

OTHER PUBLICATIONS

International Publication No. WO 90/09003 published Aug. 9, 1990.

International Publication No. WO 89/12223 published Dec. 14, 1989.

Gratton et al, "Near–Infrared Optical Spectroscopy of Tissues Using an Led Frequency Domain Spectrometer", pp. 212–216, 1994.

Patterson et al., Applied Optics, 1 Nov. 1991, vol. 30, No. 31, "Frequency–domain reflectance for the determination of the scattering and absorption properties of tissue".

METHOD AND APARATUS FOR DETERMINING AN ANALYTE IN A BIOLOGICAL SAMPLE

BACKGROUND OF THE INVENTION

1. Field of the Invention

The invention relates to a method and an apparatus for determining the concentration of an analyte in a biological sample.

The term "biological sample" refers to a body fluid or a tissue of a living organism. Biological samples in most cases are optically heterogeneous, i.e. they contain a large number of scattering centres at which irradiated light is scattered. In the case of biological tissue, in particular skin tissue, the scattering centres are formed by the cell walls and other heterogeneously optical components contained in the tissue.

Body fluids, in particular blood, are likewise optically heterogeneous biological samples, because they contain particles on which the primary radiation is scattered. Milk and other fluids subject to testing by food analysts often also contain a high concentration of scattering centres, for example in the form of emulsified fat droplets.

2. Description of the Related Art

For the qualitative and quantitative analytical determination of components of such biological samples, generally reagents or reagent systems are used that react chemically with the respective component. The reaction leads to a physically detectable change in the reaction solution, for example a change in its color, which can be measured as a measurement variable. By calibration with standard samples of known concentration, a correlation between the values of the measurement variable measured at different concentrations and the concentration is obtained. These methods, although permitting analyses of high accuracy and sensitivity, require that a liquid sample, in particular a blood sample, be taken from the body for analysis ("invasive analysis"). This sampling is unpleasant and painful and leads to a certain risk of infection.

A large number of methods and apparatuses have therefore been proposed for the in vivo and non-invasive determination of analytes in blood, tissue or other biological samples.

SUMMARY OF THE INVENTION

The invention relates to a group of such methods in which measurement light is irradiated by means of irradiation means as primary light at an irradiation site through an interface bounding the sample into the sample and light emerging out of the biological sample through an interface bounding the sample is detected by means of detection means at a detection site at a predetermined measuring distance, in order to determine (without the use of reagents) a physical property of the light which varies due to the interaction with the biological sample and which correlates with the concentration of the analyte in the biological sample. Such a method step is referred to below as a "detection step".

The physical property of the light that is determined (detected) in a detection step and correlates with the analyte concentration, which can also be referred to as a "quantifiable parameter", will for the sake of simplicity be referred to below as the "measurement variable". This term must not, however, be taken to mean that a particular amount of the measurement variable in a corresponding measurement unit has to be measured.

Insofar as the methods do not allow an absolute measurement, a calibration is required (as with the conventional methods of analysis based on chemical reactions). Customarily in at least one calibration step the measurement variable is determined on a biological sample with a known analyte concentration, which step is performed with the same measurement techniques as the detection step.

In an evaluation step of the analytical method the analyte concentration is determined from the measurement variable measured with at least one detection step, optionally in comparison with at least one calibration step. The evaluation step comprises an evaluation algorithm in which the concentration is calculated in a predetermined manner from the results of at least one detection step and as a rule at least one calibration step.

The wavelengths of the light which are discussed for such methods generally lie between some 300 nm and several thousand nm, that is to say in the spectral region between near UV and infrared light. The term "light" must not be understood as a limitation to the visible spectral region of light.

The invention is based on the problem of providing a method for determining the concentration of analytes in a biological sample which operates reagent-free and non-invasively and permits good analytical accuracy, for example for observing the variation in the analyte concentration over a sufficient period of time (continuous monitoring).

The problem is solved by a method for the analytical determination of the concentration of an analyte in a biological sample, in which in a detection step light of a light transmitter is irradiated by means of irradiation means irradiated into the sample at an irradiation site as primary light through an interface bounding the biological sample and light emerging out of the biological sample through an interface bounding the sample is detected as secondary light at a detection site at a predetermined measuring distance from the irradiation site by means of detection means, in order to determine as a measurement variable a measurable physical property of the light which varies due to the interaction with the biological sample and which correlates with the concentration of the analyte in the biological sample and in an evaluation step the analyte concentration is determined on the basis of the measurement variable measured in the detection step, which is characterized in that in the detection step, (a) without movement of the light irradiation means or the detection means, frequency domain spectroscopy measurements are carried out with at least two different measurement light paths between the irradiation site and the detection site, (b) each of the frequency domain spectroscopy measurements is carried out with at least two different wavelengths of light, and (c) there is determined with each of the frequency domain spectroscopy measurements the phase shift of the secondary light compared with the primary light together with an intensity measurement variable.

The intensity measurement variable is preferably either the DC-intensity component of the secondary light or the AC-intensity component of the secondary light. The biological sample is in particular a biological tissue, specifically a skin tissue, in particular of the finger pads, the upper abdominal walls, the nail bed, the lip, the tongue or the inner upper arm of the person or muscular tissue or subcutaneous adipose tissue or the tissue of the sclerae.

Frequency-domain spectroscopic measuring methods (frequency domain spectrometry) are characterized in that the intensity of the primary light is modulated with a high-frequency modulation frequency (typically between 50 MHz and several GHz). The measurement variable is not—as with conventional spectroscopy—exclusively the static intensity of the secondary light, but at least one dynamic measurement variable, in particular the phase shift and the AC-amplitude of the modulated secondary light compared with the primary light is measured.

Frequency-domain spectroscopic measuring methods are used conventionally in particular for determining the mean lifetime of fluorescent dyes in analytical methods which are based on providing the analyte with a fluorescent labelling by means of a specific binding reaction. In some of such methods the fluorescence lifetime is determined as a measurement variable ("phase fluorometry"). In order to be able to determine the very short lifetimes (of the order of magnitude of less than 100 psec), radio frequency (RF)-modulated spectrometers have been developed, which operate on the basis of an intensity modulation of the light at a frequency between about 50 MHz and several GHz.

An important example of a measuring method according to this principle is the heterodyne method, in which the signal received by the light receiver (detector) is mixed with a second periodic signal whose frequency differs from the first signal by a small fraction of its modulation frequency (e.g. a few kHz). The resulting differential signal can be processed and measured comparatively simply with a lock-in amplifier or other narrow-band-selective amplification methods. An effective apparatus for such measurements is described in J. R. Lakowicz et al.: "2-GHz frequency-domain fluorometer", Rev. Sci. Instrum., 57 (1986), 2499–2506. A method for analysing glucose by means of phase-modulation fluorometry is known from J. R. Lakowicz and B. Maliwal: "Optical sensing of glucose using phase-modulation fluorometry", Analytica Chimica Acta, 271, (1993) 155–164. This refers to an in-vitro test, in which the sample is taken invasively in the conventional manner and has to be mixed with the necessary reagents, which contain a fluorescent label.

A recently developed instrument in this field is described in: A. Duncan et al. "A multiwavelength, wide band, intensity modulated optical spectrometer for near infrared spectroscopy and imaging", Proc. SPIE 1888 (1993), 248–257.

The above publications describe numerous details concerning the measurement techniques which, as the following explanations will show, can also be used to advantage in the present invention.

The frequency-domain spectroscopic measurements are performed with a plurality of different measurement light paths within the sample between the irradiation site and the detection site. It is essential that the different measurement light paths are provided without moving parts, in particular without movement of the light irradiation means or the detection means. It has been found that the possibility of a sufficiently accurate determination of the absorption parameter and the scattering parameter in biological samples, in particular skin tissue, depends critically on the fact that the variation of the distance between the irradiation site and the detection site is not realized by movement of the irradiation means and/or the detection means.

In the context of the invention there are determined in the detection step (whose test results are processed in the evaluation step to the desired analytical result) at least eight measurement values (phase difference and intensity measurement value for at least two measurement light paths and two wavelengths of light respectively). Preferably the analytical result is not determined directly from the latter, but instead separate parameters are determined from the at least eight measurement values, one of which is a measure of the scattering of the light (scattering parameter) and the other a measure of the optical absorption of the light (absorption parameter) in the biological sample. The term "scattering parameter" refers in this context primarily to the scattering coefficient and the term "absorption parameter" primarily to the optical absorption coefficient. In the context of the invention, it is, however, not required to calculate these parameters quantitatively in conventional measurement units. Instead it is sufficient to determine two independent parameters reproducibly, which are independent of one another in the sense that the scattering parameter is characteristic only of the scattering in the sample (i.e. independent of the optical absorption of the sample) and the absorption parameter is dependent only on the optical absorption in the sample (i.e. independent of the scattering).

Suitable methods for the separate determination of the scattering coefficient and the absorption coefficient in an optically heterogeneous matrix are described in the previously published literature, in particular in:

M. S. Patterson et al.: "Frequency-domain reflectance for the determination of the scattering and absorption properties of tissue", APPLIED OPTICS, 30, pp. 4474–4476 (1991 and Gratton et al.: "Near-infrared optical spectroscopy of tissues using an LED frequency domain spectrometer", Advances in Optical Imaging and Photon Migration, Technical Digest, 1994, pp. 212–215.

These publications and the methods for the determination of the absorption coefficient and the scattering coefficient described therein are based on a particular mathematical-physical concept, namely diffusion theory. The evaluation step, in which the analyte concentration is derived from the at least eight measurement values, can, however, also be carried out purely empirically by means of a mathematical correlation algorithm. Suitable methods of numerical mathematics are available, in which the measurement values as input variables can be combined with the analytical result as output variables. These include iterative methods for the optimal description of the correlation of input variables and output variables. Multilinear and non-linear algorithms can be used to combine several factors with one another and to assign them to a sole output variable or a reduced number of output variables. This allows also to take additional account of other influencing factors (such as the temperature at the measuring site).

For such methods a learning process based on a calibration is required, in which analogous detection steps are performed on biological samples with a known analyte concentration. The data set obtained (measurement values of the measurement variable in relation to the analyte concentration) is used to develop a mathematical algorithm with which the measurement values (input variables) are combined with the analytical results (output variables). After calibration has taken place, the analytical results can be determined from the measurement values with the use of this algorithm. Suitable methods, for example also in the form of neural networks, are known and commercially available as computer programs.

The movement-free setting of the various measurement light paths is according to a first preferred embodiment achieved by detecting light emerging at different individual detection sites with a plurality of detection means, wherein the detection sites have different measuring distances from at least one irradiation site. There are two possibilities for this.

Firstly, the light emerging at several different detection sites can be passed to a common light receiver via light-conducting optical elements (in particular optical fibres). The switch-over preferably is by means of an optical switch.

Secondly, a plurality of light receivers can be used, which detect the secondary light emerging at the various detection sites separately, wherein these light receivers can either be arranged directly at the detection site or else be connected to the latter by light-conducting elements. This possibility, which will be referred to below as PDOLS (plural detector one light source), appears disadvantageous at first sight, because the signals generated by each light receiver have to be amplified and processed separately, whereas if several different measuring distances are realized with only one light receiver and several assigned light transmitters whose light is irradiated at several different irradiation sites (referred to below as PLSOD for "plural light source one detector"), only the plurality of light transmitters have to be activated one after the other, which seems far less complicated electronically.

In the context of the invention it has been found that—in particular in consideration of the special measures described here—it is not only possible to realise a measurement setup using the PDOLS principle at justifiable expense of measurement instrumentation, but that special advantages are thereby achieved with respect to the determination of measurement variables correlating with an analyte in biological samples. In particular it proves to be highly advantageous that the variation in time of the tissue-optical parameters (absorption parameter and scattering parameter) is detected simultaneously at several detection points. In contrast, the PLSOD principle is, because of its sequential method of measurement, in addition to the unavoidable local variation of the tissue, also influenced by the variation in time of said tissue. These fluctuations in time can be so rapid that it is hardly possible to eliminate them during a PLSOD measurement by rapid switching of the light transmitters (within the limits set by the instrumentation).

According to a second preferred embodiment the movement-free setting of the different measurement light paths is realized by modulating the primary light with different modulation frequencies with an unchanged measuring distance between the irradiation site and the detection site. The variation of the modulation frequency leads—as will be explained in greater detail below—to changes of the measurement light path in the sample, which can be used alternatively or in addition to changes of the measurement distance to select different measurement light paths without moving parts.

In the detection step at least two frequency-domain spectroscopic measurements are carried out, each with at least two different wavelengths of the primary light. In this respect the method is similar to conventional spectroscopic methods, in particular to the "two-wavelength spectroscopy", in which a first measurement wavelength is selected in such a way that the analyte provides as strong an absorption as possible, while a second wavelength is selected as a reference wavelength in such a way that the light absorption depends as little as possible on the analyte concentration. Of course, also a plurality of wavelengths can be used for the individual detection steps, the spectrum being evaluated in known manner, for example by methods of multivariate analysis. There is also the possibility of determining a plurality of analytes. Important analytes are in particular glucose, bilirubin, cholesterol, triglyceride, urea, uric acid, oxyhaemoglobin, haemoglobin and cytochromoxidase.

According to a further preferred embodiment the invention can be used to observe the changes in the concentration of an analyte that has been added before as an exogenic substance to the investigated tissue. For example, a dye which is detectable as an analyte according to the invention can be administered intravenously. A substance which influences the scattering parameter can also be used with advantage. Such embodiment can be used with advantage for example in so-called clearance tests (functional tests on organs) or for therapy monitoring (checking of the storage and metabolic conversion of therapeutic agents in the body). The exogenic substance can also serve for the detection of pathological structures in the tissue by contrast improvement.

The concentration of glucose as an analyte is preferably derived from the scattering parameter. The connection between the concentration of glucose and the scattering in an optically heterogeneous biological sample is explained in greater detail in the PCT application PCT/DE 93/01058. The separation of the influences of the optical absorption and the scattering in the context of the present invention permits the absolute measurement of a scattering parameter and hence the absolute measurement of changes in the glucose concentration. Due to the separation of the influence of the absorption, interference due to highly absorbent substances in the sample, for example haemoglobin, is negligible. Consequently a more exact determination of the glucose concentration is possible on the basis of a scattering parameter which is free of influences of absorption in the sample.

According to a second main aspect, which is preferably applied in combination with the first main aspect (insofar as it relates to tissue), but also has independent importance, the invention is directed towards a method for the analytical determination of the concentration of an analyte in a biological sample, in which in a detection step light is irradiated into the tissue as primary light from a light transmitter through an interface bounding the biological sample and light emerging out of the biological tissue through an interface bounding the latter is detected as secondary light by a light receiver at a predetermined measuring distance, in order to determine a measurable physical property of the light as a measurement variable which varies due to the interaction with the biological sample and which correlates with the concentration of the analyte in the tissue, and in an evaluation step the analyte concentration is determined on the basis of the measurement variable measured in the detection step, which is characterized in that the light path in the tissue is adjusted to a predetermined partial volume of the tissue in which the analyte concentration is to be determined.

The light path in the biological sample can be adjusted to a predetermined partial volume by a suitable choice of measuring distance and modulation frequency in a defined manner, as will be explained in greater detail below.

BRIEF DESCRIPTION OF THE DRAWINGS

The invention will be explained in greater detail below by means of embodiments shown diagrammatically in the figures, where.

DETAILED DESCRIPTION OF THE PREFERRED EMBODIMENTS

Figure 1:
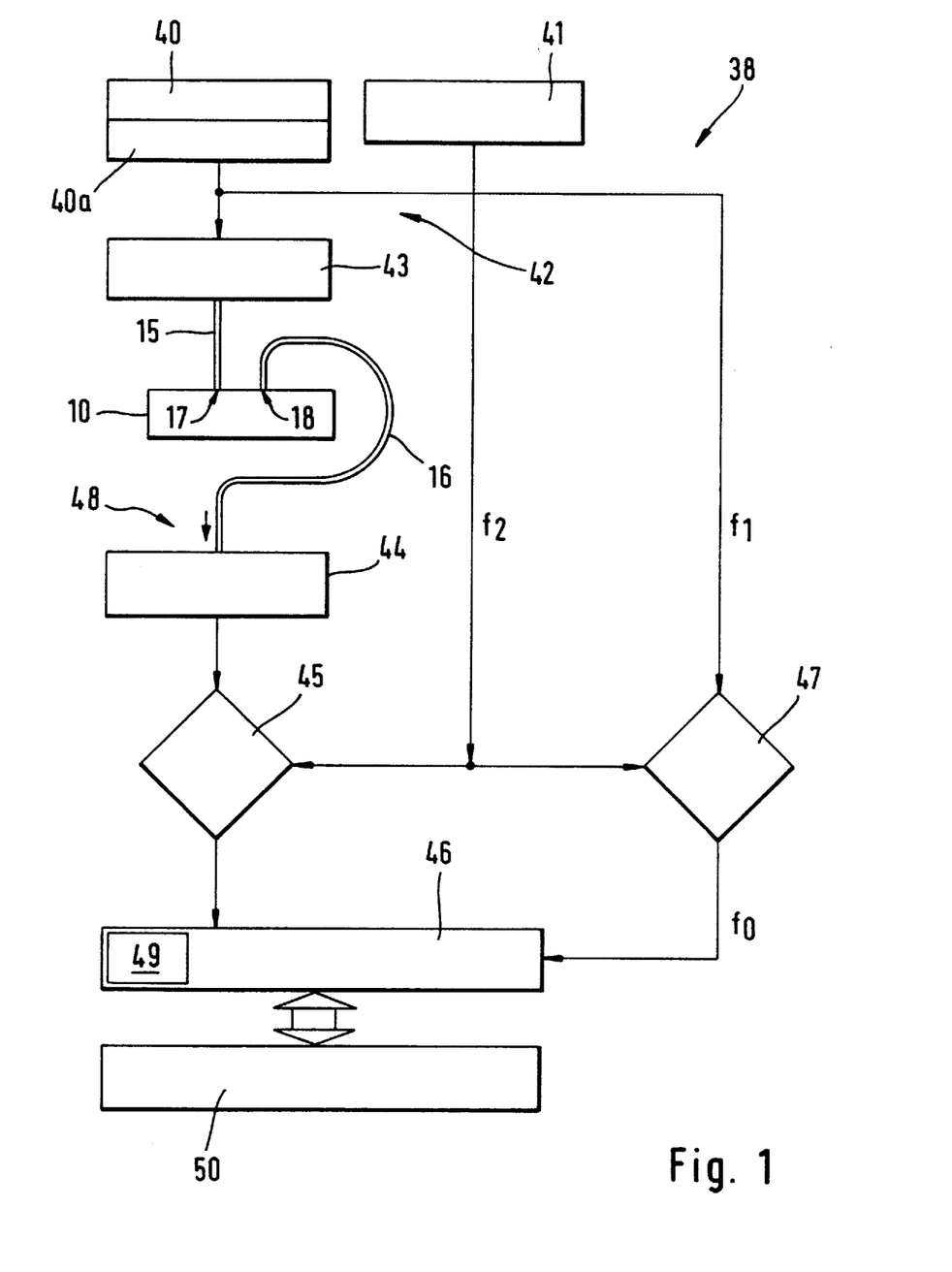
FIG. 1 shows a block diagram of a measurement and evaluation apparatus suitable for the invention.

FIG. 1 shows a block diagram of the layout of an example of a measuring device 38 for the FD spectroscopic measurement of the phase shift P and the intensity measurement variables AC and DC. The measurement principle of the embodiment shown (heterodyne method) is also used in phase fluorometry.

A frequency generator 40 generates a high-frequency periodic oscillation with which a light transmitter 43, for example a light emitting diode, is activated via an amplifier circuit (driver stage) 40a. In this way the primary light leaving the light transmitter 43 is modulated with a high frequency $f_1$, which is termed the carrier frequency. The frequency should be higher than 50 MHz, preferably above 200 MHz. The light of the light transmitter 43 is irradiated as primary light into the biological matrix 10 along a first glass fibre light guide 15 at an irradiation site 17. The light irradiation means 42 formed by the components 40, 40a, 43 and 15 can also be embodied in another manner. Various possibilities are known from numerous publications.

The light emerging from the biological sample 10 at a detection site 18 is detected with detection means 48, which comprise in the embodiment shown a detection light guide 16 through which the secondary light is transmitted to a light receiver (detector) 44. The light receiver generates an electrical output signal corresponding to the light intensity, which is coupled to a signal mixer 45. Simultaneously the output signal of a second frequency generator 41 is passed to the signal mixer 45. This frequency generator is synchronized with the frequency generator 40 and has an output frequency $f_2$ which differs only slightly (for example by $f_0 = 1$ kHz) from the frequency $f_1$ of the first frequency generator 40. The difference frequency $f_0$ is so chosen that it is well suited to synchronize a lock-in amplifier and the inherent noise of the necessary pre-amplifiers is small.

The output signal of mixer 45 is passed to the input of a lock-in amplifier 46. Lock-in amplifier 46 receives as a reference signal the mixed signal of the frequency generators 40 and 41, mixed by a second mixer 47.

Lock-in amplifier 46 generates two output signals which correspond to the real part and the imaginary part of the periodic mixed signal. From these the phase difference, the AC amplitude and the DC amplitude can be calculated, referred in each case to the reference signal. The arithmetic unit 49 required for such calculation is shown symbolically in the figure as part of the lock-in amplifier. In practice all mathematical operations will be performed by a microcomputer of the system.

The measuring instrument can also be realized in another manner. Numerous variants of electronic circuits for measuring the phase shift and the AC and DC intensity measurement variables are known and can be used in the present invention. Reference is made in this connection in particular to publications on phase fluorometry and on frequency-domain spectroscopy (including the articles by Lakowicz and Duncan cited above).

For the performance of the evaluation step required for calculating the concentration (i.e. for the execution of an evaluation algorithm), evaluation means 50, preferably in the form of the mentioned microcomputer, are provided. The evaluation means comprise in general those parts of an analytical instrument which serve to determine the desired analytical values from measured values of the measurement variables.

In the embodiment shown in FIG. 1 only one measuring distance between the irradiation site 17 and the detection site 18 is provided. Here, the adjustment of different measurement light paths within the biological sample 10 takes place by variation of the modulation frequency (carrier frequency), as will be explained in greater detail below by means of FIGS. 9 to 11.

Figure 2:
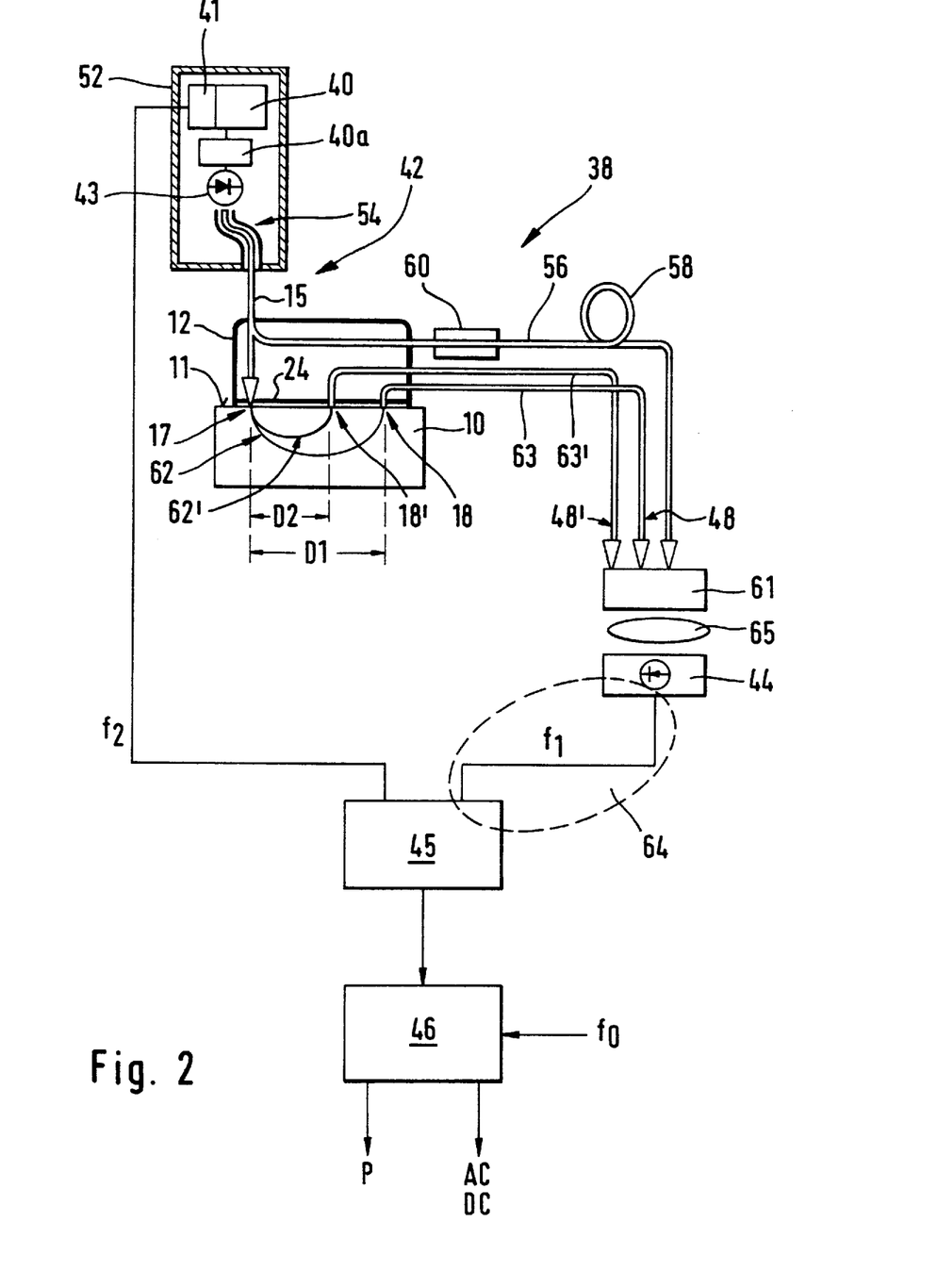
FIG. 2 shows a block diagram of a further embodiment of a measurement and evaluation apparatus suitable for the invention.

FIG. 2 shows an embodiment in which emerging light is detected with a plurality of detection means at different detection sites, wherein the detection sites have different measuring distances from a common irradiation site. In addition with reference to FIG. 2 a number of preferred instrument design features are explained which can be used singly or in combination with one another to meet particular conditions which have to be observed in carrying out the invention. As explained, the known measurement methods for determining the phase difference and the AC and DC intensity measurement variables can in principle be used in the context of the invention. The application of such methods for the analysis of biological samples nevertheless gives rise inter alia to the following problems, which cause difficulties in designing a corresponding system.

On the one hand the required measuring accuracy is very high. For example, the phase shift between the irradiated primary light and the detected secondary light must be measured with an accuracy of typically 0.1° at a frequency of the order of magnitude of 100 MHz. For continuous detection the phase angle must remain the same drift-free with integration times of a few minutes over the entire measuring period.

Preferably semiconductor light transmitters such as light emitting diodes or laser diodes are used as light transmitters. These generate primary light of very low intensity, and this results in a very low power of the light received by the light receiver of the order of magnitude of nW ($10^{-9}$ Watt).

The measuring instrument is to be as small, compact and favourably priced as possible. The instrumental requirements are therefore as far as possible to be fulfilled without expensive special components.

A first special feature of the measuring instrument 38 shown in FIG. 2 consists in the fact that the two frequency generators 40, 41, the driver stage 40a and the primary light source 43 (preferably a laser diode) are arranged in an electromagnetically insulated housing 52. The electromagnetic insulation of the housing 52 also comprises the leading out of the primary light. The light guide 15 is led out of the case 52 through a channel (high-frequency trap, RF trap) 54 which is practically impermeable to electromagnetic high-frequency radiation. Thereby the high-frequency signals generated inside the housing 52 (which are of the order of magnitude of 10 mW) do not interfere with the highly sensitive phase measurement. It is most preferred if all above-mentioned components are located in an electromagnetically insulating housing (for example a fully enclosed metal box). At least the driver stage 40a and the primary light source 43, and preferably also the frequency generator 40 controlling the latter, should be shielded electromagnetically in this way.

In the embodiment shown the housing 52 is located outside the measuring head 12 butting against the interface 11 of the sample 10 with a contact plate 24. It can however also be integrated therein.

A second special feature of the phase measuring instrument 38 shown in FIG. 2 is a reference light path 56, through which the light generated by the primary light source 43 can pass as an alternative to a sample light path 63, which includes the measurement light path 62 leading through the biological sample 10, to the same light receiver 44. The reference light path 56 comprises in the embodiment shown an optical delay section 58 (for example realized as a light guide of light-conducting fibres) and an optical attenuator 60. These elements are so dimensioned that the reference light path 56 is adjusted to the sample light path 63, the attenuation and delay of the light on the sample light path being mainly determined by the measurement light path 62 within the biological matrix. The adjustment is such that both the intensity and the transit time of the light leaving the primary light source 43 and reaching the light receiver 44 on one of the light paths 56, 63 are as similar as possible. Preferably the attenuation and delay in the reference light path 56 is adjusted to the mean values occurring in practice with the given measurement light path 62 under measurement conditions. The deviation of the light intensity should be not more than ±50%. The delay on the reference light path 56 should be matched with the delay on the sample light path 62 to such an extent that the phase shift on both paths differs by not more than ±15°, preferably ±5°. According to current experimental results the adjustment of the light paths requires a delay section 58 which is roughly four times as large as the geometrical distance (measuring distance) between the irradiation site 17 and the detection site 18. The delay section is defined by the difference of the length of the reference light path 56 compared with that part of the sample light path 63 which runs outside the sample (i.e. sample light path 63 minus measurement light path 62).

The reference light path 56 can be made highly stable with relatively simple means. Thereby an enhanced measuring accuracy—regarding changes in phase caused by changes in the analyte concentrations—can be achieved with relatively simple and hence cost-effective means. It is important that the sample light path 63 and the reference light path 56 are switchable by optical means onto the same light receiver 44. This is accomplished in the shown embodiment by means of an LCD-optical switch 61 and a lens 65.

The LCD-optical switch 61 serves in the shown embodiment also for the activation of two different measurement light paths 62 and 62' in the biological sample 10. A measuring distance D2, which is smaller compared with the measuring distance D1, with a corresponding measurement light path 62', is set by feeding the light emerging at the detection site 18' on a further sample light path 63' (preferably with the aid of a light-guide fibre) to the same LCD-optical switch 61. Thus the light-guide fibres of the sample light paths 63 and 63' form, in combination with elements common to both sample light paths (optical switch 61, lens 65 and light receiver 44), two different detection means 48, 48' for the detection of secondary light which leaves the biological matrix at the two different detection sites 18 and 18'. With this embodiment, the same phase measuring apparatus 38 can be used to determine the measurement variables phase difference (P), AC amplitude (AC) and DC amplitude (DC) for different measuring distances and (if the preferred embodiment discussed here is used) an optical reference light path 56. It may be advantageous to provide in the sample light path 63', which transports the signal of stronger intensity, an optical attenuator (not shown) and/or a delay section (also not shown), in order to adjust the intensity and phase of the signals travelling to the light receiver 44 to one another and—if the shown embodiment with an additional reference light path is realized—to the reference signal.

A third special feature of the embodiment shown in FIG. 2 consists in the fact that the signal path 64 between the light receiver 44 and the signal mixer 45 is very short. In the context of the invention it has been found that the sensitivity of the light detection is thereby influenced positively. If the signal path on the section between the components 44 and 45 is as short as possible the line capacitance is low. In this way it is possible, despite the high frequencies required, to operate with a relatively high impedance of the mixer or alterntively of a signal pre-amplifier connected in series with the latter. This in turn is advantageous with respect to the signal strength with a given current of the photodiode. Thus by simple means the effective sensitivity of the intrinsically simple and hence cost-effective semiconductor photoreceiver can be enhanced considerably.

Preferably the length of the signal path between the light receiver 44 and the mixer 45 is less than 1 cm. Particularly preferably the light receiver 44 and the signal mixer 45 are integrated together on the same semiconductor substrate. This allows advantageous circuit engineering designs. An amplifier with a mixer connected on the load side (e.g. a "balanced mixer") can be used. An FET mixer can be used, to whose gate the light receiver 54 is directly coupled. Finally, a photo-diode used as a photoreceiver can itself form part of the mixer 45. For example, one of the diodes of a balanced mixer can be replaced by the photodiode.

The light receiver 44 is particularly preferably an avalanche-type photodiode. A preferred possibility, in particular in combination with an avalanche-type photodiode, is to modulate the sensitivity of the light receiver 44 directly with the frequency $f_2$. In the case of a photomultiplier $f_2$ can be applied to its dynode. In the case of a semiconductor light receiver the supply voltage can be modulated with $f_2$. In this way the functions of the light receiver 44 and the mixer 45 are combined in one component.

The geometrical conditions regarding the dimensions of the irradiation site 17 and the detection site 18, regarding the arrangement of these sites on the interface 11 of the biological matrix 10 and in particular regarding the measuring distance D can be determined empirically in each individual case. The following basic rules should be observed.

The terms "irradiation site" and "detection site" are to be understood geometrically, namely as the sub-domain of the interface of a biological matrix in which light which in the respective detection step is critical for the determined transit time parameter passes through the interface. The numerical values given below for distances between the irradiation site and the detection site refer to the centre of the respective irradiation site or detection site, measured in the direction of the distance (i.e. of the shortest connection) between the irradiation site and the detection site.

In order to be able to assign the measurement variables with good resoluation to a particular measuring distance, the dimension of the irradiation site and the detection site in the direction of the above-mentioned distance should not be too great. Preferably it is less than 2 mm, particularly preferably less than 1 mm.

The measurement light paths of the measurements which are made in a detection step and the results of which are used to determine an absorption parameter and/or scattering parameter, should differ sufficiently from one another. In general it can be said that the difference must be such that the measuring error in the determination of the individual measurement values (for different measurement light paths) is substantially smaller than the difference of the measurement values. Preferably the intensity measurement values used to calculate an absorption parameter or a scattering parameter should differ by at least 10%. The difference of the measurement light paths should correspond to this requirement.

The greatest possible measuring distance is determined by the decreasing intensity of the secondary light and the resulting deterioration in the signal/noise ratio. The upper limit can be determined empirically in each individual case. Preferably the measuring distance should be less than 4 cm. According to the current findings an optimum measuring accuracy is achieved with measuring distances of about 2 cm (somewhere between 1 cm and 3 cm).

FIGS. 3 to 7 show advantageous details of a PDOLS measuring apparatus.

Figure 3:
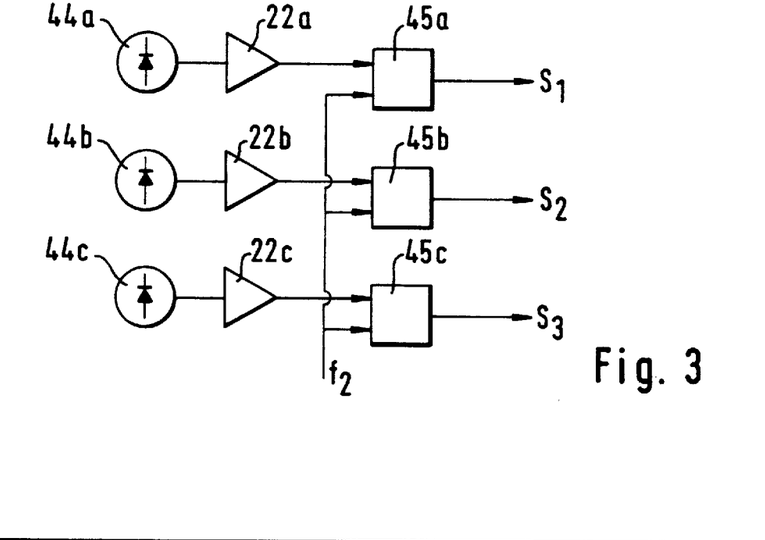
FIG. 3 shows a part of a circuit for a measuring apparatus according to the PDOLS principle.
Figure 4:
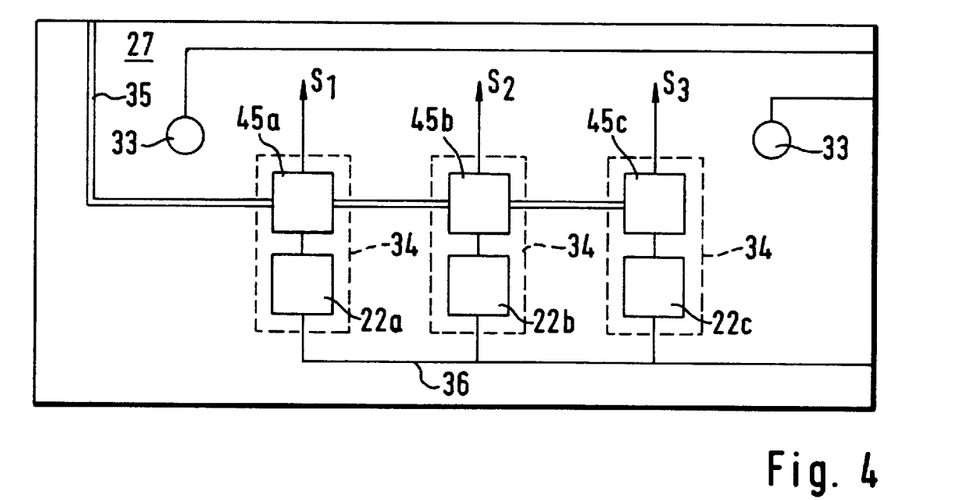
FIG. 4 shows a top view of the circuit board of a measuring apparatus according to the PDOLS principle.

According to FIG. 3 a high-frequency pre-amplifier 22a, 22b, 22c is connected to the output of each light receiver 44a, 44b, 44c. The output signal of the high-frequency amplifiers 22a, 22b, 22c is fed in each case to a signal mixer 45a, 45b, 45c, to whose other input the frequency $f_2$ (of a circuit according to FIG. 1) is applied. The signal paths between the light receivers and the high-frequency pre-amplifiers as well as between the high-frequency pre-amplifiers and the signal mixers should be as short as possible for the reasons already discussed. Preferably the overall length of the signal path from the light receiver to the mixer is less than 1 cm, particularly preferably less than 3 mm. The output signals $S_1$, $S_2$, $S_3$ of the mixers 45a, 45b, 45c are of low frequency and can consequently be processed with the conventional means of low-frequency circuit engineering.

Figure 5:
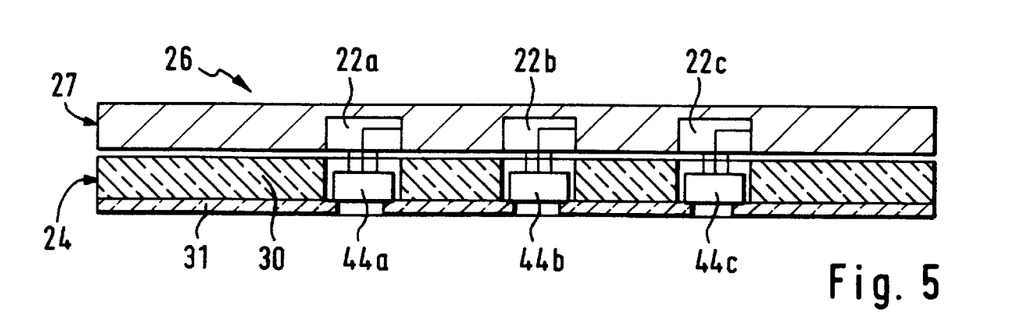
FIG. 5 shows a side view of a circuit board of FIG. 4 and a contact plate.
Figure 6:
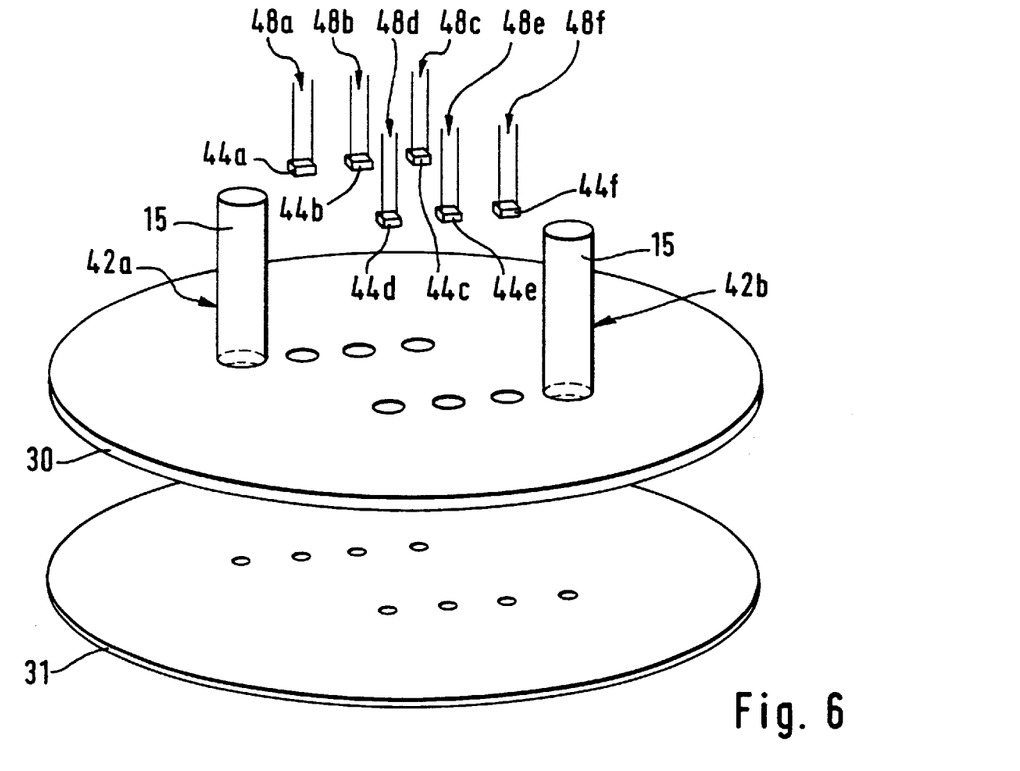
FIG. 6 shows an exploded view of an alternative embodiment of the contact plate of a measuring head suitable for the invention.

FIGS. 5 and 6 show the contact plate 24, which is pressed against the boundary surface 11 of the biological sample 10 to perform an analysis. The contact plate 24 forms part of a carrier component 26 which carries all the light receivers 44a, 44b and 44c. The carrier component 26 comprises in addition to the contact plate 24 an electronic board 27, which is a multilayer circuit board. It can be constructed as a printed circuit board or in hybrid technology. The contact plate 24 is likewise of multilayered construction and consists of a plate of black tinted glass ("black glass plate") 30 and a metal plate 31. Avalanche-type photodiodes are disposed in matching recesses of the black glass plate 30 as light receivers 44, whose light-sensitive surface is turned towards the sample.

The electronic board 27 of the carrier component 26 serves as a carrier for the HF pre-amplifiers 22a, 22b, 22c and the signal mixers 45a, 45b, 45c. The pre-amplifier 22 and the mixer 45 assigned to a light receiver 44 are located in a metal screening case 34. The high frequency $f_2$ is coupled to the mixers 45a, 45b, 45c via a 50 Ohm line constructed as a strip bus, which runs in the electronic board 27. The supply voltage for the avalanche-type photodiodes is fed along a line 36 likewise running in the electronic board 27. The further circuitry for the processing of the low-frequency signals is preferably also accommodated on the electronic board, but is not shown for the sake of clarity.

Two temperature measuring elements are thermally coupled to the electronic board 27 of the carrier component 26. They are used to monitor the temperature of the carrier component 26. Thus changes in the sensitivity of the light receiver 44 which are caused by temperature fluctuations can be taken into account in the determination of the absorption or scattering parameter and in the evaluation step in general.

Due to the common integration of the light receivers 44a, 44b, 44c in a single component, preferably together with the necessary pre-amplifiers and the mixers, all the avalanche-type photodiodes have the same relative phase position and the processing channels of the detection means for the various detection sites have very largely identical characteristics. In addition a compact design is obtained. The multilayer technique makes shielded feeding of the high-frequency signals possible and permits a very short connection between the light receivers and the mixers. If FET mixers are used, the separate pre-amplifier can be omitted. In this case the distance between each light receiver and the mixer assigned to it should be minimal.

FIG. 6 shows in the form of an exploded drawing the arrangement of two irradiation means 42a, 42b and six detection means 48a to 48f in the contact plate of a measuring instrument.

The contact plate consists, as in the embodiment of FIG. 5, of a black glass plate 30 and a metal plate 31. The black glass plate has recesses which are adapted to the size of the elements inserted therein. The figure shows transmitter light guides 15 as a part of irradiation means 42a, 42b, through which light from a light transmitter (not shown in the figure) can be irradiated to two different irradiation sites 17a, 17b. The size of the irradiation site is determined by the diameter of the corresponding openings in the metal plate 31 and preferably is less than 1 mm, particularly preferably to about 0.5 mm.

In the shown embodiment the light receivers 44a to 44f are arranged without interposed light-conducting fibres directly on the surface of the contact plate 24, which is in contact with the sample. They sit in corresponding recesses of the black glass plate 30. The size of the corresponding detection sites 18a to 18f is in turn determined by the size of the openings in the mask 32. This is preferably less than 2 mm, particularly preferably about 1 mm. The use of several irradiation means and several detection means, in an arrangement in which the same measuring distance can be set by several different combinations of irradiation sites and detection sites, permits a redundant measurement, as is explained in the WO 94/10901 already cited.

Figure 7:
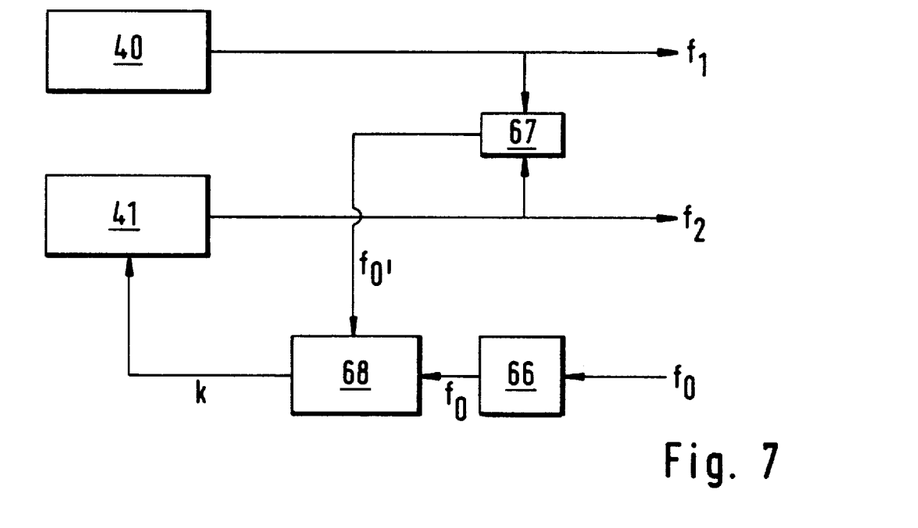
FIG. 7 shows a part of a circuit representing a preferred embodiment of the frequency stabilization for two frequency generators for generating a constant difference frequency.

For the accuracy of the phase measurement with a phase measuring instrument operating on the heterodyne principle it is most important that the difference frequency $f_0$ between the two frequency generators ($f_1$, $f_2$) 40 and 41 ("cross correlation frequency") remains constant over the measurement period. On the other hand $f_0$ (for example 1 kHz) constitutes only a small fraction of the absolute frequencies of the frequency generators 40, 41 (for example 100.00 MHz and 100.001 MHz), and therefore highly stable and hence expensive oscillators would have to be used in the frequency generators 40, 41.

According to an alternative preferred embodiment of the invention the difference frequency $f_0$ is preselected by a difference frequency generator 66. On the basis of the preselected difference frequency the frequency of the second measurement frequency generator $f_2$ is controlled in such a way that the second frequency generator 41 follows frequency fluctuations of the first frequency generator 40 with a constant difference frequency.

In the embodiment according to FIG. 7 this principle is realized in that the frequencies $f_1$ and $f_2$ of the generators 40, 41 are applied to the inputs of a signal mixer 67 at whose output the current difference frequency $f_0'$ is generated. The latter is fed as an actual signal to a control unit 68 to which on the other side the signal of the difference frequency generator 66 is fed as nominal signal. The control unit 68 compares the actual signal $f_0'$ with the nominal signal $f_0$ and generates a correction signal k, which is fed to one of the two frequency generators (in the figure to the frequency generator 41), in order to control its frequency $f_2$ in such a way that the difference between $f_1$ and $f_2$ corresponds exactly to the preselected difference frequency $f_0$. The control takes place preferably in a known manner on the PLL principle.

Possibilities for modifying the light path within a biological sample 10 without moving parts will be explained by means of FIGS. 8 to 11.

Figure 8:
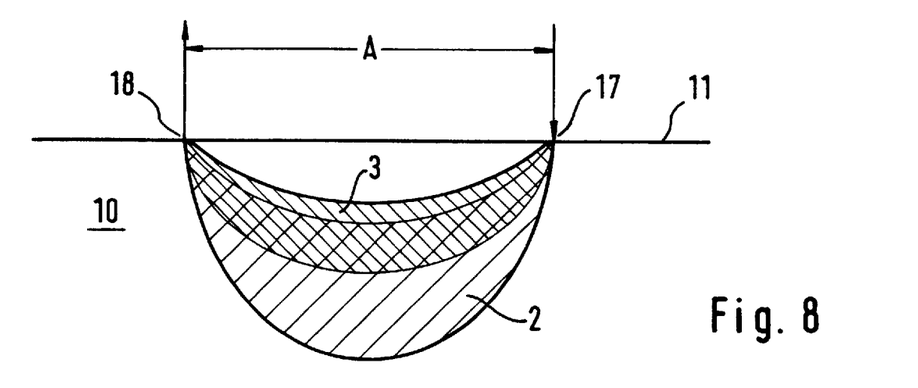
FIG. 8 shows the effective light path in a biological tissue for two different modulation frequencies.

FIG. 8 shows in a cross-sectional view the optical light path in a biological sample 10 for two different modulation frequencies $f_1$ and $f_2$, wherein the light path with the lower modulation frequency $f_1$ is shown as 2 and the light path with the higher modulation frequency $f_2$ as 3. The light is irradiated in each case at the same irradiation site 17 of the surface 11 with a light irradiation means (not shown) and measured at the same detection site 18 of the surface 11, so that the measuring distance A is the same in both cases.

The "effective optical path" in the tissue can for example be defined as the partial volume of the sample in which a particular percentage (e.g. 90%) of the light travels, which passes from the irradiation site 17 to the detection site 18 and contributes to the electrical signal generated by the light receiver. Because of the geometrical conditions produced in the sample by the multiple scattering, this volume has a roughly banana-shaped form if the irradiation point and the light source lie (as shown) on the same surface 11 of the tissue sample 10.

The form of the effective optical light path is a complex function of the measuring distance between the irradiation site 17 and the detection site 18, the absorption and scattering properties of the sample (including their possible local differences) and the modulation frequency. It can be stated as a general rule, however, that the maximum depth of the optical path 2, 3 in the tissue becomes greater with increasing distance A and with decreasing frequency f, while it conversely becomes smaller if a smaller measuring distance and a higher frequency are used. On the basis of this information, by coordinating the measuring distance A and the modulation frequency f, the light path may be adjusted in the sample in such a way that it passes essentially in a predetermined (desired) partial volume of the tissue.

Figure 9:
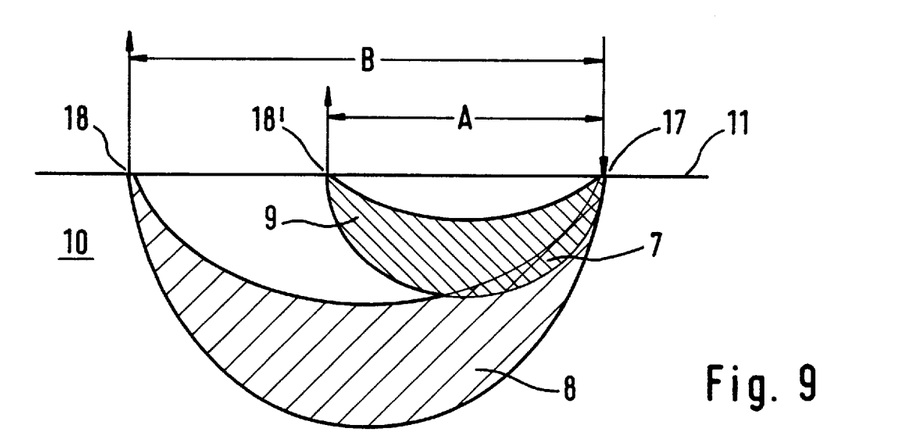
FIG. 9 shows the effective light path in a biological tissue for two different measuring distances and an identical modulation frequency.

FIG. 9 shows two light paths 8, 9 for identical modulation frequencies, but different measuring distances A and B, wherein in the case shown the light is irradiated at an irradiation site 17 and detected at two different detection sites 18, 18'. It becomes apparent that according to the general rule explained above the maximum depth of the light path is greater with the greater measuring distance B. The two light paths overlap only in a relatively small partial volume 7. This is disadvantageous for many applications, because the measured measurement variables refer to different measurement volumes.

Figure 10:
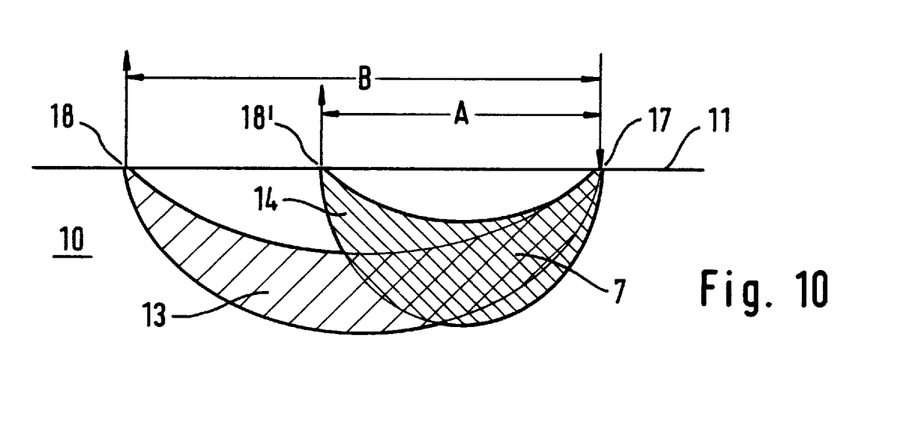
FIG. 10 shows the effective light path in a biological tissue for different measuring distances and modulation frequencies optimized for maximum overlapping and FIG. 11 shows the optical light path in a biological tissue with the use of a reflective surface in contact with the tissue surface between the irradiation point and the detection point.

In this respect the possibility shown in FIG. 10 is more advantageous, namely to use with different measuring distances A and B simultaneously a higher modulation frequency for the greater measuring distance (light path 13) than for the shorter measuring distance B (light path 14). Thereby a far greater overlapping volume 7 is obtained.

By suitable choice of the measuring distance and the modulation frequency it is therefore possible, in particular in layered structures such as the skin, to adjust the effective light path so that mainly a particular layer is measured. According to recent findings it may be advantageous to concentrate the measurement not primarily on the skin tissue, but on the underlying fatty or muscular tissue.

Figure 11:
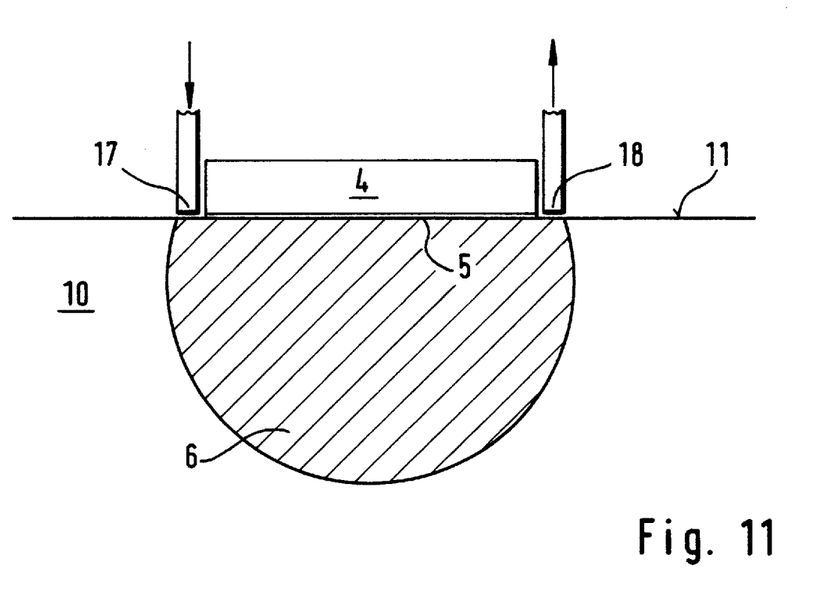

A further possibility for influencing the effective light path is shown in highly diagrammatic form in FIG. 11. In this case a component 14 with a reflective surface 5 is in contact with the tissue surface 11 and extends between the irradiation site 17 and the detection site 18. This can technically be realized e.g. by a reflective coating of the contact plate pertaining to the sensor measuring head and supported on the tissue surface 11. Light components travelling to the surface 11 of the sample 10 are reflected back into the tissue by the reflective surface 5 and hence contribute to the signal detected at the detection site 18, so that the shown form of the effective optical light path 6 is obtained, which includes the volume right up to the surface 11. This measure can also be used with advantage to adjust the light path in the tissue to a desired predetermined partial volume.

It becomes clear that different measurement light paths can be set in the biological sample 10 by variation of the modulation frequency with a given position of the irradiation site and the detection site (and unchanging measuring distance). In addition it is possible to choose the partial volume in which the effective measurement light path travels. The choice of the partial volume in the tissue can be of considerable importance for the measuring accuracy in in-vivo analyses. In particular, the measurement should be limited as precisely as possible to a predetermined partial volume of the skin, in order to reduce various effects caused by the heterogeneity of different tissue layers. A concentration of the measurement on the capillary base of the skin is particularly preferred.

We claim:

1. A method for the analytical determination of a concentration of an analyte in a biological sample, said method comprising the steps of:

performing at least two detection measurements, each detection measurement comprising the step of irradiating light at an irradiation site as primary light into the biological sample through a boundary surface thereof, said light being propagated along a light path within the biological sample, and detecting light as the light emerges from the biological sample as secondary light through a detection site at the boundary surface, said irradiation site and said detection site being separated by a predetermined measuring distance;

wherein said at least two detection measurements are carried out with at least two different measurement light paths between the irradiation site and the detection site, said at least two different measurement light paths being provided by a plurality of detection sites with a plurality of detection means, each of said plurality of detection sites having different measuring distances from the irradiation site, each of said at least two detection measurements is a frequency-domain spectroscopic measurement being performed at at least two different wavelengths of light, and wherein each frequency-domain spectroscopic measurement includes a comparison of a phase shift of the secondary light with the primary light as a first measurement variable and an intensity of the secondary light as a second measurement variable, said method further comprising a step of determining an analyte concentration in the biological sample based upon the first and second measurement variables.

2. A method as recited in claim 1, wherein said determining step includes determining at least one of an absorption parameter which is a measure of an optical absorption of the light in the biological sample and a scattering parameter which is a measure of scattering of the light in the biological sample, said absorption parameter and said scattering parameter being respectively determined as measurement quantities independent of each other, and wherein said determining step determines the analyte concentration from one of the parameters.

3. A method as recited in claim 2, wherein the concentration of the analyte is determined based upon the absorption parameter.

4. A method as recited in claim 3, wherein the analyte Is at least one analyte from the group consisting of water, glucose, bilirubin, cholesterol, triglyceride, urea, uric acid, oxyhemoglobin, hemoglobin, and cytochromoxidase.

5. A method as recited in claim 2, wherein the concentration of the analyte is determined based upon the scattering parameter.

6. A method as recited in claim 2, wherein said biological sample includes an exogenic substance to influence one of the scattering parameter and the absorption parameter in the sample, and wherein said step of determining the analyte concentration comprises observation of a change of a concentration of said exogenic substance.

7. A method as recited in claim 1, wherein the second measurement variable is an AC intensity component of the secondary light.

8. A method as recited in claim 1, wherein the second measurement variable is a DC intensity component of the secondary light.

9. A method as recited in claim 1, wherein said primary light is modulated with varying modulation frequencies, said varying modulation frequencies resulting in differing measurement light paths for at least one measurement distance between the irradiation site and one of the detection sites.

10. A method as recited in claim 1, wherein said biological sample comprises blood.

11. A method as recited in claim 1, wherein said biological sample comprises biological tissue.

12. A method as recited in claim 11, wherein said biological tissue comprises one from the group consisting of skin tissue, finger pad, upper abdominal walls, nail bed, lip, tongue, inner upper arm, muscular tissue, subcutaneous adipose tissue, and tissue of the sclerae of a human.

13. A method as recited in claim 1, wherein each detection measurement comprises irradiating light at the irradiation site as primary light into the biological sample through a boundary surface thereof, and detecting light at a plurality of different detection sites through a corresponding plurality of light paths, and further including a step of optically switching light from the plurality of light paths onto a common light path.

14. A method for the analytical determination of a concentration of an analyte in a biological sample, said method comprising the steps of:

performing at least two detection measurements, each detection measurement comprising the step of irradiating light at an irradiation site as primary light into the biological sample through a boundary surface thereof, said light being propagated along a light path within the biological sample, and detecting light as the light emerges from the biological sample as secondary light through a detection site at the boundary surface, said irradiation site and said detection site being separated by a predetermined measuring distance;

wherein said at least two detection measurements are carried out with at least two different measurement light paths between the irradiation site and the detection site, the at least two different measurement light paths in the biological sample being directed to a selected volume of the sample where an analyte concentration is desired to be determined, each of said at least two detection measurements is a frequency-domain spectroscopic measurement being performed at at least two different wavelengths of light, wherein each frequency-domain spectroscopic measurement includes a comparison of a phase shift of the secondary light with the primary light as a first measurement variable and an intensity of the secondary light as a second measurement variable, said method further comprising a step of determining the analyte concentration in the biological sample based upon the first and second measurement variables.

15. A method as recited in claim 14, wherein the selected volume of the biological sample comprises a capillary base of skin of a patient.

16. A method as recited in claim 15, further comprising a step of supporting a reflective surface on a biological sample, in order to adjust the selected volume.

17. A method as recited in claim 14, further comprising a step of supporting a reflective surface on the biological sample, in order to adjust the selected volume.

18. A method as recited in claim 14, wherein said primary light is modulated with varying modulation frequencies, said varying modulation frequencies resulting in differing measurement light paths for at least one measurement distance between the irradiation site and the detection site, and said varying modulation frequencies and the measuring distances are coordinated to direct the light path through a selected volume of the biological sample.

19. A method as recited in claim 14, wherein said determining step includes determining at least one of an absorption parameter which is a measure of an optical absorption of the light in the biological sample and a scattering parameter which is a measure of scattering of the light in the biological sample, said absorption parameter and said scattering parameter being respectively determined as measurement quantities independent of each other, and wherein said determining step determines the analyte concentration from one of the parameters.

20. A method as recited in claim 19, wherein the concentration of the analyte is determined based upon the absorption parameter.

21. A method as recited in claim 20, wherein the analyte is at least one analyte from the group consisting of water, glucose, bilirubin, cholesterol, triglyceride, urea, uric acid, oxyhemoglobin, hemoglobin, and cytochromoxidase.

22. A method as recited in claim 19, wherein the concentration of the analyte is determined based upon the scattering parameter.

23. A method as recited in claim 19, wherein said biological sample includes an exogenic substance to influence one of the scattering parameter and the absorption parameter in the sample, and wherein said step of determining the analyte concentration comprises observation of a change of a concentration of said exogenic substance.

24. A method as recited in claim 14, wherein the second measurement variable is an AC intensity component of the secondary light.

25. A method as recited In claim 14, wherein the second measurement variable is a DC intensity component of the secondary light.

26. A method as recited in claim 14, wherein said biological sample comprises blood.

27. A method as recited in claim 14, wherein said biological sample comprises biological tissue.

28. A method as recited in claim 27, wherein said biological tissue comprises one from the group consisting of skin tissue, finger pad, upper abdominal walls, nail bed, lip, tongue, inner upper arm, muscular tissue, subcutaneous adipose tissue, and tissue of the sclerae of a human.

29. An apparatus for analytical determination of a concentration of an analyte in a biological sample, said apparatus comprising:
  a measuring head for engaging a surface of the biological sample;
  irradiation means attached to said measuring head for irradiating primary light into the biological sample at an irradiation site on the surface of the biological sample, said irradiation means including a light transmitter;
  detection means for detecting secondary light emerging from the biological sample at a detection site through the surface of the biological sample, said detection means including a light receiver, said detection means being connected to said measuring head;
  first frequency generator means connected to said irradiation means for modulating the primary light with a first high-frequency modulation;
  phase measuring means connected to said detection means for determining a phase shift measurement variable of the secondary light with respect to the primary light;
  intensity measuring means connected to said detection means for determining an intensity measurement variable of the secondary light; and
  evaluation means connected to said phase measuring means and said intensity measuring means for determining an analyte concentration of the biological sample from an output of the phase measuring means and the intensity measuring means,
  wherein the output of the phase measuring means and the output of the intensity measuring means are generated without movement of the irradiation means and the detection means, and are based upon two different measurement light paths between the irradiation site and the detection site; said apparatus further comprising
  driver means connected to said first frequency generator means for driving the light transmitter; and
  an electromagnetically insulating housing for electromagnetically insulating the driver means and the light transmitter.

30. An apparatus according to claim 29, wherein said evaluation means comprises a scattering parameter determining means for determining a scattering parameter as a measure of scattering of the primary light in the biological sample.

31. An apparatus according to claim 29, wherein said evaluation means includes an absorption parameter determining means for determining an absorption parameter as a measure of an optical absorption of the primary light in the biological sample.

32. An apparatus according to claim 29, wherein said intensity measuring means includes AC amplitude measuring means for measuring an AC amplitude of the secondary light as the intensity measurement variable.

33. An apparatus according to claim 29, wherein said intensity measuring means includes DC amplitude measuring means for measuring an DC amplitude of the secondary light as the intensity measurement variable.

34. An apparatus according to claim 29, wherein said first frequency generator means is disposed in said housing.

35. An apparatus as recited in claim 29, said apparatus further comprising a second frequency generator means for generating a second high-frequency modulation, said second frequency generator means disposed in said housing.

36. An apparatus for analytical determination of a concentration of an analyte in a biological sample, said apparatus comprising:
  a measuring head for engaging a surface of the biological sample;
  irradiation means attached to said measuring head for irradiating primary light into the biological sample at an irradiation site on the surface of the biological sample, said irradiation means including a light transmitter;
  detection means for detecting secondary light emerging from the biological sample at a detection site through the surface of the biological sample, said detection means including a light receiver, said detection means being connected to said measuring head;
  first frequency generator means connected to said irradiation means for modulating the primary light with a first high-frequency modulation;
  phase measuring means connected to said detection means for determining a phase shift measurement variable of the secondary light with respect to the primary light;
  intensity measuring means connected to said detection means for determining an intensity measurement variable of the secondary light; and
  evaluation means connected to said phase measuring means and said intensity measuring means for determining analyte concentration of the biological sample from an output of the phase measuring means and the intensity measuring means,
  wherein the output of the phase measuring means and the output of the intensity measuring means are generated without movement of the irradiation means and the detection means, and are based upon two different measurement light paths between the irradiation site and the detection site; said apparatus further comprising
  a plurality of said detection means, each detection means of said plurality of detection means simultaneously detecting light emerging from the biological sample at different detection sites.

37. An apparatus according to claim 36, wherein said evaluation means comprises a scattering parameter determining means for determining a scattering parameter as a measure of scattering of the primary light in the biological sample.

38. An apparatus according to claim 36, wherein said evaluation means includes an absorption parameter measurement means for determining an absorption parameter as a measure of an optical absorption of the primary light in the biological sample.

39. An apparatus according to claim 36, wherein said intensity measuring means includes AC amplitude measuring means for measuring an AC amplitude of the secondary light as the intensity measurement variable.

40. An apparatus according to claim 36, wherein said intensity measuring means includes DC amplitude measuring means for measuring an DC amplitude of the secondary light as the intensity measurement variable.

41. An apparatus as recited in claim 36 wherein said plurality of detection means includes a plurality of light receivers disposed on a common carrier.

42. An apparatus as recited in claim 41, said apparatus further comprising:

temperature measuring means coupled to said common carrier for measuring a temperature of said common carrier, said temperature measuring means generating an output signal, said temperature measurement means being connected to said evaluation means, wherein said evaluation means determines the concentration of the analyte based partially upon the output signal of the temperature measurement means.

43. An apparatus as recited in claim 41, wherein said common carrier comprises a multilayer circuit board.

44. An apparatus as recited in claim 36, wherein said apparatus comprises a plurality of detection means for detecting light emerging from the biological sample, each of said plurality of detection means detecting light at different detection sites through a corresponding plurality of light paths; said apparatus further comprising:

optical switching means for optically switching the plurality of light paths onto a common light receiver, wherein said plurality of detection means are attached to said measuring head.

45. An apparatus for analytical determination of a concentration of an analyte in a biological sample, said apparatus comprising:

a measuring head for engaging a surface of the biological sample;

irradiation means attached to said measuring head for irradiating primary light into the biological sample at an irradiation site on the surface of the biological sample, said irradiation means including a light transmitter;

detection means for detecting secondary light emerging from the biological sample at a detection site through the surface of the biological sample, said detection means including a light receiver, said detection means being connected to said measuring head;

first frequency generator means connected to said irradiation means for modulating the primary light with a first high-frequency modulation;

phase measuring means connected to said detection means for determining a phase shift measurement variable of the secondary light with respect to the primary light;

intensity measuring means connected to said detection means for determining an intensity measurement variable of the secondary light; and evaluation means connected to said phase measuring means and said intensity measuring means for determining an analyte concentration of the biological sample from an output of the phase measuring means and the intensity measuring means, wherein the output of the phase measuring means and the output of the intensity measuring means are generated without movement of the irradiation means and the detection means, and are based upon two different measurement light paths between the irradiation site and the detection site; said apparatus further comprising high-frequency amplifying means connected to said detection means, said high-frequency amplifying means for amplifying an output of the light receiver, wherein a connection distance between the light receiver and the high-frequency amplifier means is minimized.

46. An apparatus for analytical determination of a concentration of an analyte in a biological sample, said apparatus comprising:

a measuring head for engaging a surface of the biological sample;

irradiation means attached to said measuring head for irradiating primary light into the biological sample at an irradiation site on the surface of the biological sample, said irradiation means including a light transmitter;

detection means for detecting secondary light emerging from the biological sample at a detection site through the surface of the biological sample, said detection means including a light receiver, said detection means being connected to said measuring head;

first frequency generator means connected to said irradiation means for modulating the primary light with a first high-frequency modulation;

phase measuring means connected to said detection means for determining a phase shift measurement variable of the secondary light with respect to the primary light;

intensity measuring means connected to said detection means for determining an intensity measurement variable of the secondary light; and evaluation means connected to said phase measuring means and said intensity measuring means for determining an analyte concentration of the biological sample from an output of the phase measuring means and the intensity measuring means, wherein the output of the phase measuring means and the output of the intensity measuring means are generated without movement of the irradiation means and the detection means, and are based upon two different measurement light paths between the irradiation site and the detection site; said apparatus further comprising signal mixer means for mixing a plurality of signals produced from the phase measuring means and the intensity measuring means, said signal mixer means being connected to an output of the light receiver, wherein a length of a signal path between the light receiver and the signal mixer means is minimized.

47. An apparatus as recited in claim 46, wherein said signal mixer means is also connected to said irradiation means.

48. An apparatus as recited in claim 46, wherein said signal mixer means comprises a FET mixer, and wherein the light receiver is connected to a gate of the FET mixer.

49. An apparatus as recited in claim 46, wherein said light receiver comprises a photodiode, and wherein said signal mixer includes said photodiode.

50. An apparatus for analytical determination of a concentration of an analyte in a biological sample, said apparatus comprising;
- a measuring head for engaging a surface of the biological sample;
- irradiation means attached to said measuring head for irradiating primary light into the biological sample at an irradiation site on the surface of the biological sample, said irradiation means including a light transmitter;
- detection means for detecting secondary light emerging from the biological sample at a detection site through the surface of the biological sample, said detection means including a light receiver, said detection means being connected to said measuring head;
- first frequency generator means connected to said irradiation means for modulating the primary light with a first high-frequency modulation;
- phase measuring means connected to said detection means for determining a phase shift measurement variable of the secondary light with respect to the primary light;
- intensity measuring means connected to said detection means for determining an intensity measurement variable of the secondary light; and
- evaluation means connected to said phase measuring means and said intensity measuring means for determining an analyte concentration of the biological sample from an output of the phase measuring means and the intensity measuring means,
- wherein the output of the phase measuring means and the output of the intensity measuring means are generated without movement of the irradiation means and the detection means, and are based upon two different measurement light paths between the irradiation site and the detection site; said apparatus further comprising
- optical reference means connected to said detection means for providing a reference light path which essentially corresponds to one of the two different measurement light paths with respect to light transit time and light intensity attenuation, and optical switching means for optically switching the light between one of the measurement light paths and the reference light path.

51. An apparatus for analytical determination of a concentration of an analyte in a biological sample, said apparatus comprising:
- a measuring head for engaging a surface of the biological sample;
- irradiation means attached to said measuring head for irradiating primary light into the biological sample at an irradiation site on the surface of the biological sample, said irradiation means Including a light transmitter;
- detection means for detecting secondary light emerging from the biological sample at a detection site through the surface of the biological sample, said detection means including a light receiver, said detection means being connected to said measuring head;
- first frequency generator means connected to said irradiation means for modulating the primary light with a first high-frequency modulation;
- phase measuring means connected to said detection means for determining a phase shift measurement variable of the secondary light with respect to the primary light;
- intensity measuring means connected to said detection means for determining an intensity measurement variable of the secondary light; and
- evaluation means connected to said phase measuring means and said intensity measuring means for determining an analyte concentration of the biological sample from an output of the phase measuring means and the intensity measuring means,
- wherein the output of the phase measuring means and the output of the intensity measuring means are generated without movement of the irradiation means and the detection means, and are based upon two different measurement light paths between the irradiation site and the detection site; said apparatus further comprising
- second frequency generator means connected to said first frequency generator means, said first and second frequency generator means being configured to oscillate with a constant difference frequency therebetween, said difference frequency being determined by a difference frequency generator means, and wherein a frequency of the second frequency generator means is controlled based upon the difference frequency to follow frequency fluctuations of the first frequency generator means.

* * * * *

UNITED STATES PATENT AND TRADEMARK OFFICE
CERTIFICATE OF CORRECTION

PATENT NO. : 5,770,454
DATED : June 23, 1998
INVENTOR(S) : Essenpreis et al.

It is certified that error appears in the above-identified patent and that said Letters Patent is hereby corrected as shown below:

On the title page, item [54], Col. 1, line 1 delete "APARATUS" and insert

APPARATUS --. Item [30], insert -- October 29, 1994, [DE]

Germany, PCT/DE 94/01290 --.

Signed and Sealed this

Fifteenth Day of September, 1998

Attest:

BRUCE LEHMAN

*Attesting Officer*     *Commissioner of Patents and Trademarks*